US00PP12449P2

(12) United States Plant Patent
Krahn et al.

(10) Patent No.: US PP12,449 P2
(45) Date of Patent: Mar. 12, 2002

(54) FLOWERING CRAB APPLE TREE NAMED 'MORNING PRINCESS'

(75) Inventors: Richard G. Krahn; Robert E. Krahn; Victor J. Krahn, all of Saskatoon (CA)

(73) Assignee: Bailey Nurseries, Inc., St. Paul, MN (US)

( * ) Notice: Subject to any disclaimer, the term of this patent is extended or adjusted under 35 U.S.C. 154(b) by 0 days.

(21) Appl. No.: 09/519,405

(22) Filed: Mar. 3, 2000

(51) Int. Cl.[7] ..... A01H 5/00
(52) U.S. Cl. ..... Plt./173
(58) Field of Search ..... Plt./173

(56) References Cited

PUBLICATIONS

Plant Varieties Journal, Government of Canada, Cover Pages, pp. 18 and 19, and FIG. 1 (Jan. 1999).

UPOV–ROM GTITM Computer Database 2001/01, Feb. 6, 2001, GTI Jouve Retrieval Software, Citation for 'Morning Princess'.*

* cited by examiner

*Primary Examiner*—Bruce R. Campell
*Assistant Examiner*—Annette Para
(74) *Attorney, Agent, or Firm*—Burns, Doane, Swecker & Mathis, L.L.P.

(57) ABSTRACT

A new and distinct variety of Siberian Crab Apple tree (i.e., *Malus baccata*) is provided. The new variety can be readily distinguished from the 'Royal Beauty' variety (non-patented in the United States). A vigorous growth habit is exhibited with strong apical dominance combined with descending side branches that are disposed at approximately 90° to the trunk at the point of attachment. The leaves are purple with green shading. Attractive red-pink flowers are formed. Very small globose fruit is formed that is purple when fully mature. The new variety is particularly well suited for growing as a distinctive ornamental plant in the landscape.

2 Drawing Sheets

SUMMARY OF THE INVENTION

The new and distinct variety of ornamental flowering crab apple tree was discovered during the late 1960's as a chance seedling growing among open-pollinated 'Sutherland' flowering Siberian crab trees (non-patented in the United States), growing in Applicants' nursery at Saskatoon, Saskatchewan, Canada. The exact parentage of the new variety is unknown. It is believed to be a Siberian Crab and to be botanically classified *Malus baccata*. In view of the distinctive appearance of the new variety it was carefully preserved and was removed to Applicants' test garden at Saskatoon, Saskatchewan, Canada where it has been continuously observed thereafter. Had the new variety of the present invention not been discovered and preserved it would have been lost to mankind.

It was found that the new variety of *Malus baccata* of the present invention exhibits the following combination of characteristics:

(a) Exhibits a vigorous growth habit with strong apical dominance combined with descending side branches that are disposed at approximately 90° to the trunk at the point of attachment, (b) Forms purple leaves with green shading, (c) Forms attractive pink-red flowers, (d) Forms very small globose fruit that is purple when fully mature, and (e) Is particularly well-suited for providing ornamentation in the landscape.

Trees of the new variety can be asexually reproduced by budding and grafting. More specifically, trees of the new variety have been budded onto Malus 'Antenouka' and 'Columbia' rootstock at Saskatoon, Saskatchewan, Canada beginning in 1995. The characteristics of the new variety have been found to be strictly transmissible from one generation to another following such asexual reproduction.

The new variety readily can be distinguished from the 'Sutherland' flowering crab apple tree which exhibits an upright growth habit, bright pink flowers, and purple leaves.

The new variety readily can be distinguished from the 'Royal Beauty' flowering crab apple tree by the maintenance of apical dominance with more or less upright branching at the crown. On the contrary the growth habit of the 'Royal Beauty' variety is full weeping.

The new variety of the present invention has been named the 'Morning Princess' variety.

BRIEF DESCRIPTION OF THE PHOTOGRAPHS

The accompanying photographs show as nearly true as it is reasonably possible to make the same in color illustrations of this character during May and mid-August, 1999, views of typical four year-old trees of the new variety. The trees were being grown at Saskatoon, Saskatchewan, Canada. The trees were two years on bud and were transplanted and grown for four years. The trees had been asexually reproduced by budding on Malus 'Columbia' rootstock.

Figure 1:
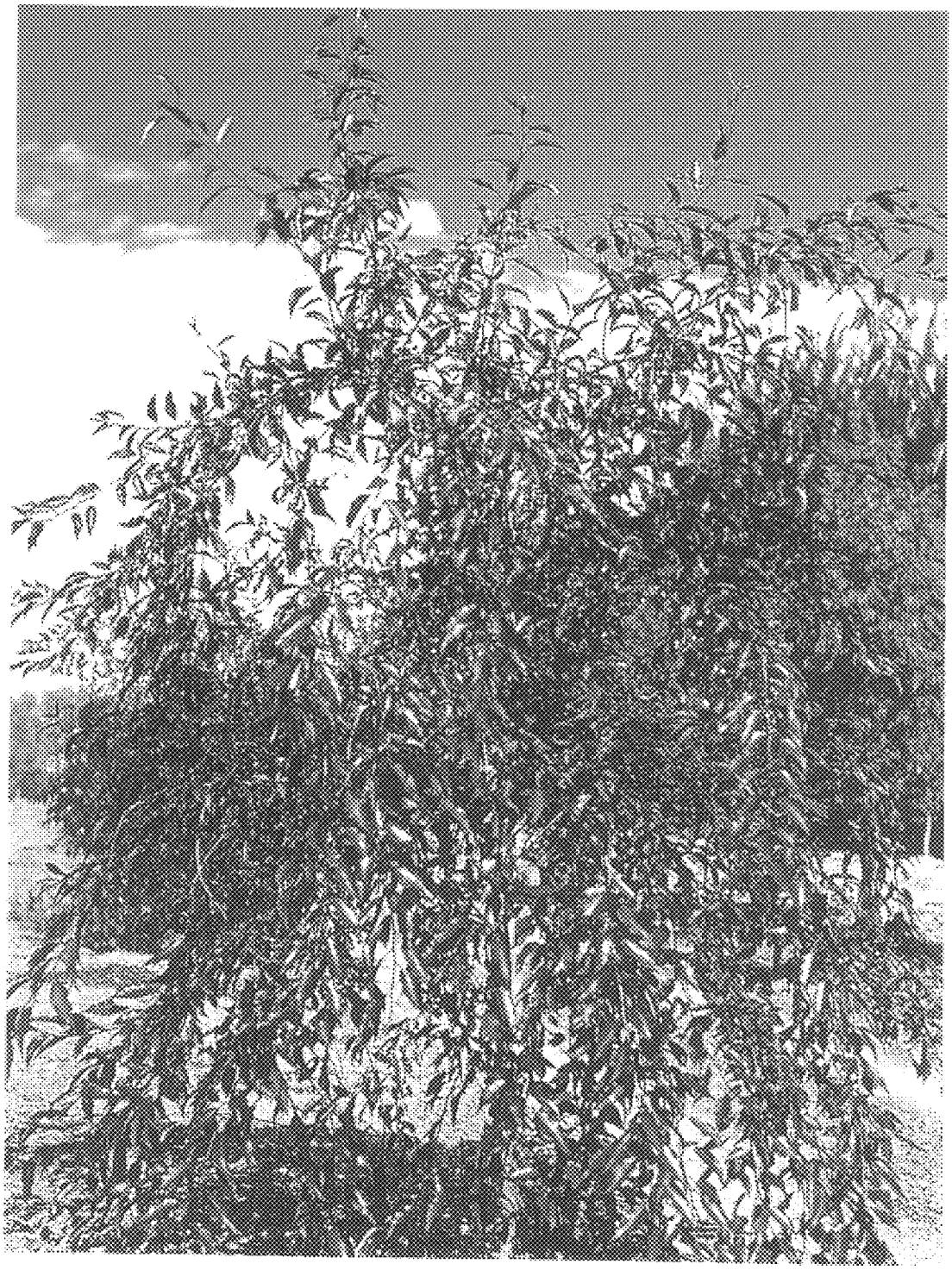

FIG. 1 illustrates a typical overall tree of the new variety during August. Many of the leaves have now assumed a coloration of green with purple shading. The drooping growth habit with strong apical dominance is apparent.

Figure 2:
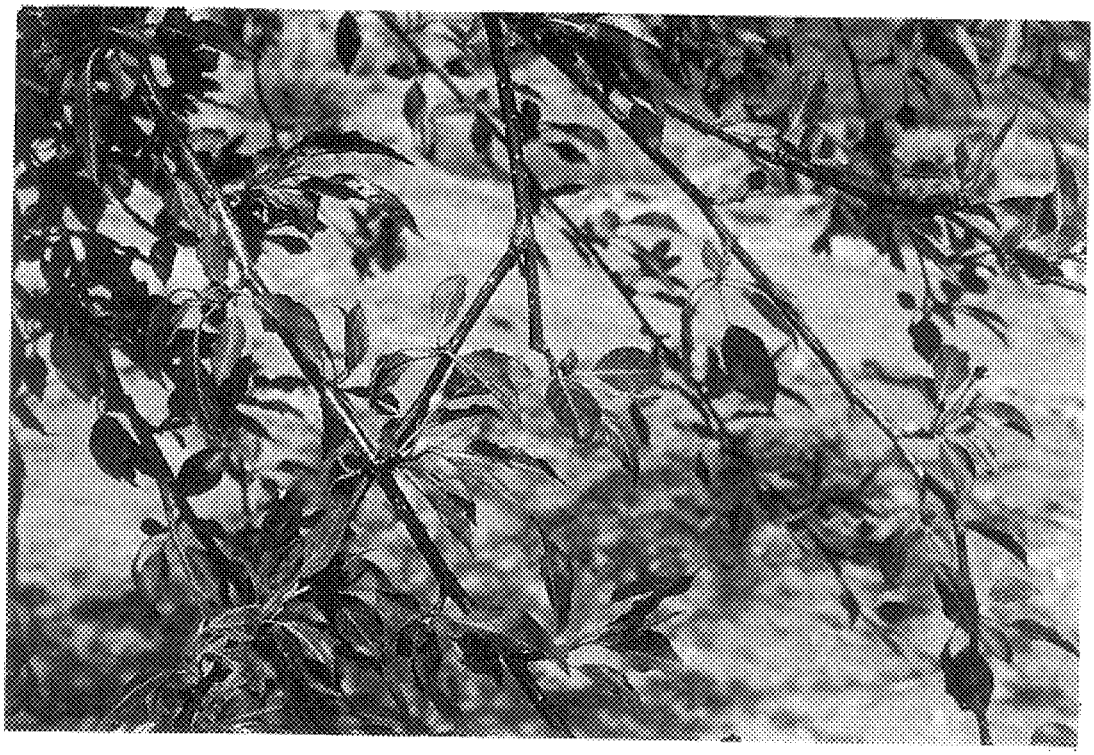

FIG. 2 illustrates typical branches and leaves of the new variety during mid- to late-May. Many of the leaves are more heavily purple in coloration. Some leaves assume more green coloration.

Figure 3:
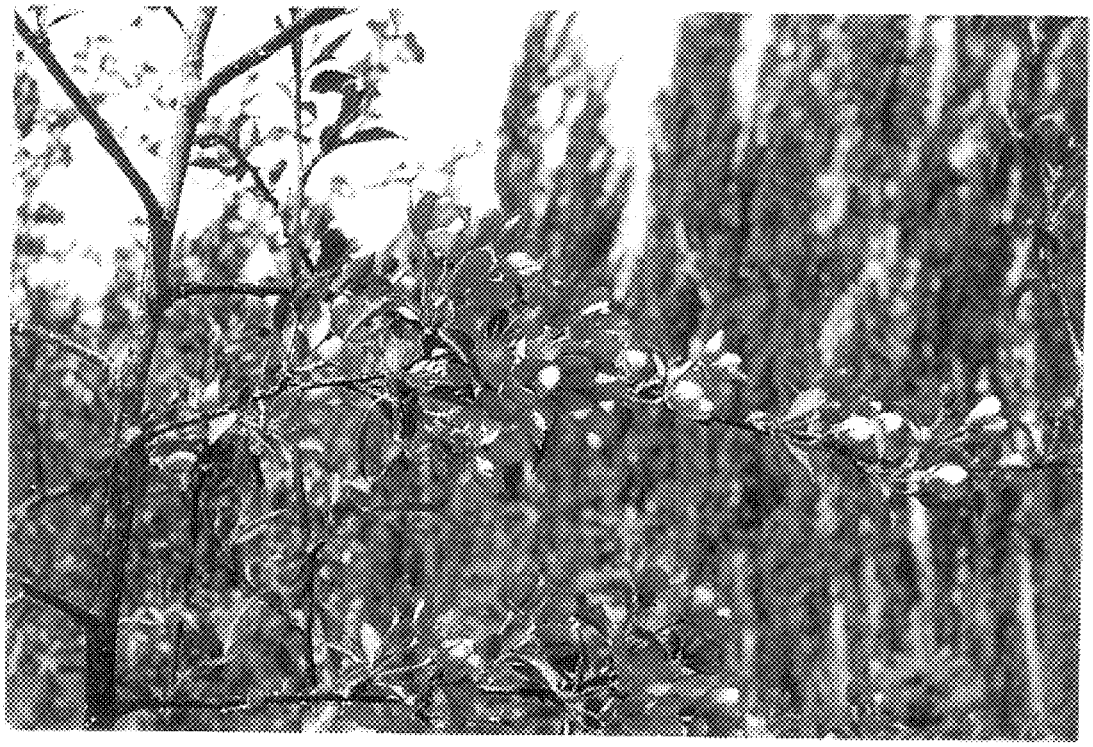

FIG. 3 illustrates typical blossoms of the new variety during mid- to late-May.

DETAILED DESCRIPTION

The chart used in the identification of color is that of The Royal Horticultural Society, London (R.H.S. Colour Chart). Other reference to color is to be accorded its customary dictionary significance. The description is based upon the inspection of trees of the new variety while budded on Malus 'Columbia' rootstock while growing during June in the landscape at Saskatoon, Saskatchewan, Canada.

Botanical classification: *Malus baccata* (L.) Borkh., cv. 'Morning Princess'.

Tree:

*Vigor.*—Initially very vigorous.

*Size.*—Trees commonly achieve a height of approximately 6 to 7 feet in two years following budding. A four year-old tree commonly achieves a height of approximately 8 feet and has a trunk diameter of 2 inches. The original tree of the new variety is approximately 15 feet in height.

*Growth habit.*—Descending or drooping side branches while maintaining strong apical dominance at the top (see the photograph). In contrast the 'Royal Beauty' variety while exhibiting drooping side branches also displays a descending top.

*Branch angle.*—The lateral side branches are disposed at approximately 90° to the trunk at the point of attachment. In contrast the lateral branches of the 'Royal Beauty' variety as disposed a less than 90° to the trunk at the point of attachment and are more drooping overall. The 'Royal Beauty' cultivar can be characterized as being fully weeping.

*Bark.*—Commonly near Greyed-Purple Group 187A in coloration on new wood with increasing furrowing and greying with age.

*Hardiness.*—Very good. Grows well in Hardiness Zone No. 2. Has not been tested in colder climates to date.

*Disease resistance.*—No fireblight damage has been observed to date.

Shoot characteristics (Dormant one year-old):

*Texture.*—Glabrous.

*Glossiness of bark.*—Weak, is dull in appearance.

*Thickness.*—Approximately ⅛ inch in diameter at center of middle internode.

*Flexibility.*—Weak.

*Length of internode.*—Approximately 20 mm. on average.

*Lenticels.*—Small in size (e.g., approximately 3 to 5 mm. in diameter on average). Presented in an irregular display.

*Color.*—Purplish, near Greyed-Purple Group 187A.

*Size of lateral buds.*—Small.

*Shape of bud tip.*—Pointed.

*Position of bud.*—Relative to the axis is conspicuously held out. This can be compared to the adpressed bud positioning of the 'Royal Beauty' variety.

Leaf characteristics:

*Shoot tip color.*—The growing tip is purple in coloration. This can be compared to green-red for the 'Royal Beauty' variety.

*Configuration of shoot tip.*—Concave. This can be compared to a convex configuration for the 'Royal Beauty' variety.

*Pubescence on shoot tip* (*upper side*).—Is absent. This can be compared to medium pubescence for the 'Royal Beauty' variety.

*Color shoot tip.*—Purple on lower side. This can be compared to purple-pink for the 'Royal Beauty' variety.

*Leaf lobes.*—Absent.

*Size.*—Medium. The length commonly ranges from 50 to 75 mm. (mean 55 mm.) and the width commonly ranges from 22 to 28 mm. (mean 25 mm.). This can be compared to a length of 55 to 80 mm. (mean 67 mm.) and a width of 30 to 40 mm. (mean 35 mm.) for the 'Royal Beauty' cultivar.

*Orientation.*—Outwards.

*Blade ratio.*—The ratio of length to width from the 4th to 6th fully expanded leaf is medium. This can be compared to large length to width ratio for the 'Royal Beauty' variety.

*Leaf shape.*—Elliptical.

*Apex shape.*—Acuminate.

*Base shape.*—Generally cuneate.

*Margin.*—Finely serrated in a regular pattern.

*Glossiness.*—The upper surface is medium glossy. This can be compared to weak glossy for the 'Royal Beauty' variety.

*Texture.*—Glabrous.

*Veins.*—Bear weak anthocyanin coloration. This can be compared to a strong anthocyanin coloration for the 'Royal Beauty' variety.

*Color.*—When fully expanded green-purple on the upper side, Greyed-Purple Group 187A with green shading, and green-purple on the underside, Greyed-Purple Group 187C with green shading. In contrast the fully expanded leaves of the 'Royal Beauty' variety are more dark green with a less intense anthocyanin coloration. Commonly the upper surface is Green Group 135A and the under surface is Greyed-Purple Group 185B for the 'Royal Beauty' variety. In the fall the leaves change to full purple, and the leaf fall tends to be late and is comparable to that of the 'Royal Beauty' variety.

*Petiole length.*—Approximately 30 to 35 mm (near 32 mm) in length and tends to be shorter than that of the 'Royal Beauty' variety. For instance, the 'Royal Beauty' commonly displays a length of 35 to 55 mm (near 50 mm).

Flower characteristics:

*Time.*—Early bud burst, and the beginning of flowering is mid-season. During 1998 bud burst occurred at April 10th to 15th.

*Color.*—Pink-red, Red Group 55A when fully open. This can be compared to purple for the 'Royal Beauty' variety.

*Pedicel.*—Red in coloration and approximately 3 to 4 mm in length.

*Size.*—Approximately 23 to 28 mm. (mean 25 mm.) in diameter when fully open. This can be compared to a 27 to 30 mm. (mean 30 mm.) diameter for the 'Royal Beauty' variety.

*Petal shape.*—Narrow-ovate. This can be compared to ovate for the 'Royal Beauty' variety.

*Petal margin.*—Entire.

Fruit characteristics:

*Size.*—Very small and commonly less than 5.5 mm. in diameter.

*Shape.*—Globose, and relatively symmetrical in side view.

*Fragrance.*—Slight.

*Sepals.*—Near Red Group 55A in coloration.

*Stamens.*—Near Yellow Group 10B in coloration.

*Pistils.*—Near Red Group 55B in coloration.

*Pollen.*—Formed in abundance and yellow in coloration.

*Ribbing.*—Absent.

*Crowning.*—Absent at distal end.

*Aperture of eye.*—Closed.

*Size of eye.*—Small.

*Persistence of calyx.*—Commonly is present in mature fruit.

*Sepals.*—Short in length, and commonly touch at base in the absence of overlap.

*Basin.*—The eye basin commonly is very shallow, and narrow in width.

*Stalk.*—Commonly is long and thin. This can be compared to a medium length for the 'Royal Beauty' variety.

*Stalk cavity.*—Commonly is narrow in depth and shallow in width.

*Surface.*—Smooth.

*Bloom of skin.*—Absent.

*Waxiness of skin.*—Absent.

*Translucency of skin.*—Absent.

*Skin thickness.*—Relatively thin.

*Skin color.*—Relatively uniform deep purple, Greyed-Purple Group 187A, with no secondary coloration when fully mature. The original glossy appearance of the fruit tends to dull with full maturity.

*Russet.*—Low in quantity and occasionally is present on the cheeks.

*Lenticels.*—Small in size, not prominent, and near Greyed-Purple Group 187A in coloration.

*Flesh color.*—Purple, Greyed-Purple Group 185B.

*Core line.*—The fruit when observed in cross-section exhibits no core line when viewed median the locules.

*Aperture of locules.*—Closed when viewed in cross-section.

*Fruit setting.*—Poor.

*Maturity date.*—Late.

*Seed color.*—Near Red Group 53A.

*Seed shape.*—Normal.

*Persistence.*—Very long with the fruit commonly remaining in place until approximately early December.

I claim:

1. A new and distinct variety of *Malus baccata* tree which exhibits the following combination of characteristics:

(a) Exhibits a vigorous growth habit with strong apical dominance combined with descending side branches that are disposed at approximately 90° to the trunk at the point of attachment, (b) Forms purple leaves with green shading, (c) Forms attractive pink-red flowers, (d) Forms very small globose fruit that is purple when fully mature, and (e) Is particularly well-suited for providing ornamentation in the landscape; substantially as herein shown and described.

* * * * *